United States Patent
Park et al.

(10) Patent No.: US 7,794,990 B2
(45) Date of Patent: Sep. 14, 2010

(54) MICROORGANISM OF CORYNEBACTERIUM GENUS HAVING ENHANCED L-LYSINE PRODUCTION ABILITY AND METHOD OF PRODUCING L-LYSINE USING THE SAME

(75) Inventors: Young Hoon Park, Seongnam (KR); Hyun Min Koo, Goyang (KR); Sang Jo Lim, Incheon (KR); Jun Ok Moon, Seoul (KR); So Yeon Rah, Seoul (KR); Young Lyeol Yang, Goyang (KR)

(73) Assignee: CJ Cheiljedang Corporation, Seoul (KR)

( * ) Notice: Subject to any disclaimer, the term of this patent is extended or adjusted under 35 U.S.C. 154(b) by 631 days.

(21) Appl. No.: 11/564,599

(22) Filed: Nov. 29, 2006

(65) Prior Publication Data
US 2007/0122890 A1    May 31, 2007

(30) Foreign Application Priority Data
Nov. 30, 2005    (KR)    ................. 10-2005-0115906

(51) Int. Cl.
*C12P 13/08*    (2006.01)
*C12N 1/21*    (2006.01)
(52) U.S. Cl. ................. 435/115; 435/252.32; 536/23.2; 536/23.7
(58) Field of Classification Search ........................ None
See application file for complete search history.

(56) References Cited

U.S. PATENT DOCUMENTS

| | | | |
|---|---|---|---|
| 6,812,006 | B2 | 11/2004 | Moeckel et al. |
| 6,872,533 | B2 | 3/2005 | Toland et al. |
| 2002/0110879 | A1* | 8/2002 | Bathe et al. ................. 435/115 |

FOREIGN PATENT DOCUMENTS

| | | |
|---|---|---|
| EP | 1108790 A2 | 6/2001 |
| JP | 2002191370 A | 7/2002 |
| WO | 02/26755 A2 | 4/2002 |

OTHER PUBLICATIONS

Ikeda, M., Nakagawa, S., The *Corynebacterium glutamicum* genome: features and impacts on biotechnological processes, Appl. Microbiol. Biotechnol., vol. 62(2-3), pp. 99-109, Aug. 2003, Epub May 13, 2003. English abstract with NCBI sequence transcription, 3 pages.

Korean Office Action issued May 21, 2007 from the Korean Intellectual Property Office with English translation, 5 pages.

Kalinowski et al., "The complete *Corynebacterium glutamicum* ATCC 13032 genome sequence and its impact on the production of L-aspartate-derived amino acids and vitamins", Journal of Biotechnology, 2003, vol. 104, pp. 5-25.

\* cited by examiner

*Primary Examiner*—Rebecca E. Prouty
(74) *Attorney, Agent, or Firm*—Rothwell, Figg, Ernst & Manbeck, pc

(57) ABSTRACT

Provided are a microorganism of *Corynebacterium* genus that has an inactivated endogenous NCgl1835 gene therein and produces L-lysine, and a method of producing L-lysine using the same.

2 Claims, 1 Drawing Sheet

MICROORGANISM OF CORYNEBACTERIUM GENUS HAVING ENHANCED L-LYSINE PRODUCTION ABILITY AND METHOD OF PRODUCING L-LYSINE USING THE SAME

CROSS-REFERENCE TO RELATED PATENT APPLICATION

This application claims the benefit of Korean Patent Application No. 10-2005-0115906, filed on Nov. 30, 2005, in the Korean Intellectual Property Office, the disclosure of which is incorporated herein in its entirety by reference.

BACKGROUND OF THE INVENTION

1. Field of the Invention

The present invention relates to a microorganism of Corynebacterium genus having enhanced L-lysine production ability and a method of producing L-lysine using the same.

2. Description of the Related Art

Microorganisms of Corynebacterium genus, particularly Corynebacterium glutamicum are gram-positive microorganisms that are used in L-amino acid production. L-amino acid, particularly L-lysine is widely used for animal feed and medical supplies, and is produced by fermentation of the microorganisms of Corynebacterium genus. As such, the microorganisms of Corynebacterium genus are important in producing L-amino acid, and thus much research on improving the method of producing L-amino acid has been conducted.

This research includes a method of developing microorganisms of Corynebacterium genus that produces L-amino acid by disrupting specific genes or attenuation expressing specific genes using recombination DNA technique. For example, U.S. Pat. No. 6,872,553 discloses a method of producing L-lysine of microorganisms of Corynebacterium genus by fermentation. The method comprises: growing microorganisms of Corynebacterium genus having an attenuated DNA encoding phosphoenol pyruvate (PEP) carboxykinase (pck) by at least one mutation selected from the group consisting of insertion mutation in which at least one base pair is inserted into the DNA, deletion mutation in which at least one base pair is deleted from the sequence of the DNA, base pair transition and transversion mutation introducing a nonsense codon in the DNA or having reduced phosphoenol pyruvate (PEP) carboxykinase (pck) activity compared with microorganisms of Corynebacterium genus that are not attenuated; concentrating desired L-amino acid product in medium or cells of the microorganism; and separating the L-amino acid.

In addition, many studies on how each gene involved in L-amino acid biosynthesis affects L-amino acid production by amplifying the genes to develop microorganisms of Corynebacterium genus have been conducted (Eggeling, Amino Acids 6, 261-272 (1994)). Also, microorganisms of Corynebacterium genus can be developed by introducing foreign genes from other bacteria. For example, Japanese Patent Publication No. hei 7-121228 discloses a method of producing L-glutamine acid and L-proline acid. The method comprises culturing microorganisms of Corynebacterium genus or Brevibacterium genus that contain recombinant construct between DNA fragment having genetic information involving synthesis of citric acid synthase and vector DNA, and producing L-glutamine acid and L-proline acid from the cultures.

However, demand for microorganisms having improved L-lysine production ability still exists.

SUMMARY OF THE INVENTION

The present invention provides a microorganism of Corynebacterium genus having enhanced L-lysine production ability.

The present invention also provides a method of producing L-lysine using the microorganism.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
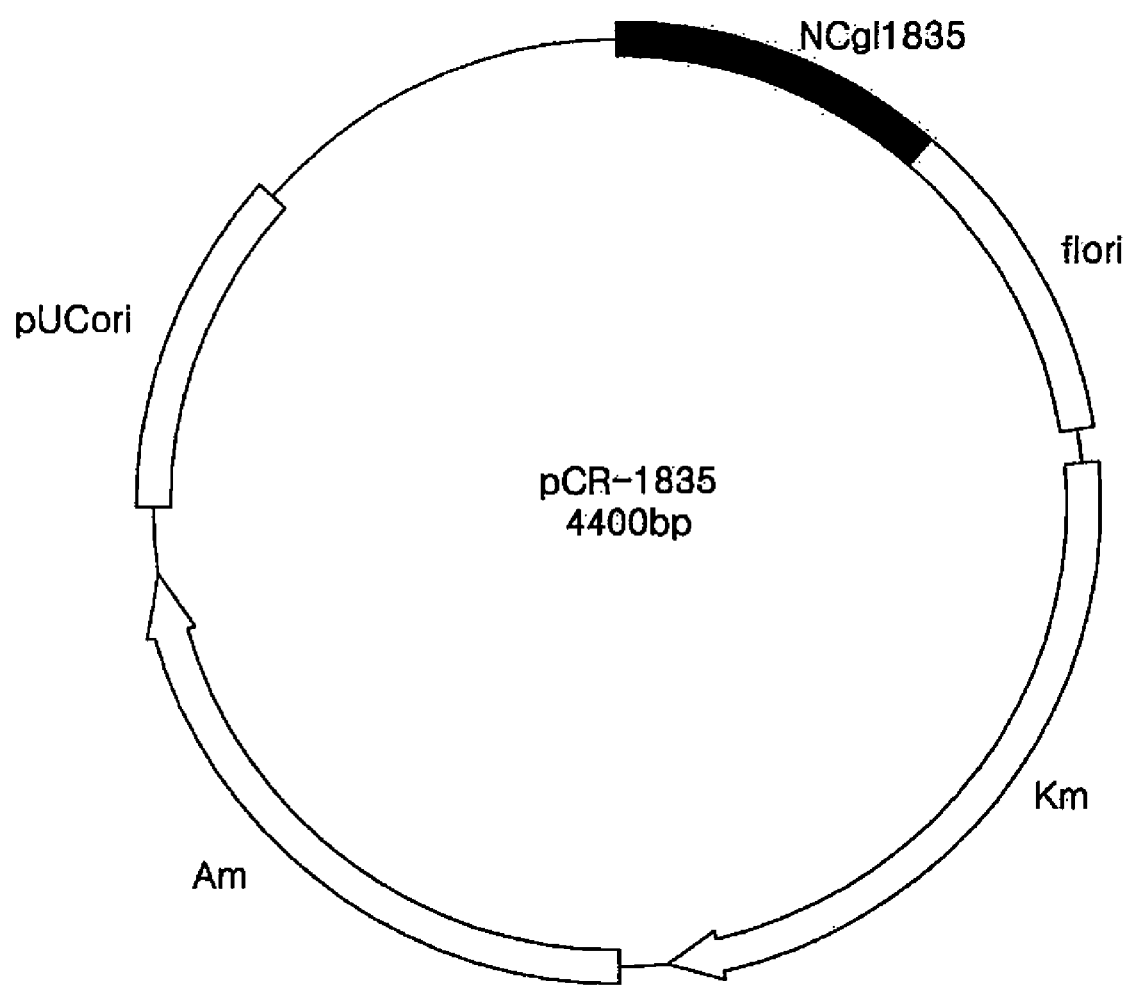
FIG. 1 is a diagram of a pCR-1835 vector in which approximately 500 bp of a NCgl1835 gene segment is cloned therein.

The present invention provides a microorganism of Corynebacterium genus that has an inactivated endogenous NCgl1835 gene therein and produces L-lysine.

In microorganism of the present invention, the endogenous NCgl1835 gene is a gene that endogenously exists in the microorganism of Corynebacterium genus, and is known as a transcription regulatory factor (EC:2.7.1.63). The activity of the gene is predicted from a complete sequence analysis of a genome of Corynebacterium glutamicum ATCC 13032. Preferably, the gene may have a nucleotide sequence of SEQ ID NO: 1.

In the microorganism of the present invention, the microorganism of Corynebacterium genus of which endogenous NCgl1835 gene is inactivated can be Corynebacterium glutamicum ATCC 13032, Corynebacterium thermoaminogenes FERM BP-1539, Corynebacterium glutamicum KFCC 10881, and Corynebacterium glutamicum KFCC 11001, but is not limited thereto.

In the present invention, the inactivation can be achieved by performing arbitrary inactivation methods known to those of skill in the art. In the present invention, the term "inactivation" intends to mean that the expression of the NCgl1835 gene is reduced to a low level compared to a wild strain or genes that are not expressed and genes that express products having no activity or reduced activity in spite of being expressed are produced.

In the microorganism of Corynebacterium genus, the inactivation can be caused by at least one mutation selected from the group consisting of insertion mutation in which at least one base pair is inserted into the NCgl1835 gene, deletion mutation in which at least one base pair is deleted from the sequence of the NCgl1835 gene, base pair transition and transversion mutation introducing a nonsense codon in the NCgl1835 gene.

In the microorganism of Corynebacterium genus, the inactivated NCgl1835 gene may be selected by transforming the microorganism of Corynebacterium genus with a vector including a part of the NCgl1835 gene and an antibiotic marker and culturing the transformed microorganism in the presence of the antibiotic marker. Preferably, the vector is a pCR-1835 vector including a NCgl1835 gene segment of SEQ ID NO: 2. The microorganism is transformed with a vector including a part of the gene sequence, and when the transformed microorganism is cultured under a selection marker, homologous recombination occurs between the part of the gene sequence and endogenous genes of the microorganism. The endogenous genes of the microorganism are recombined by the homologous recombination, and among the recombined genes, only recombinants including the antibiotic marker are selected by the selection marker. As a result, a microorganism of *Corynebacterium* genus of which endogenous NCgl1835 gene is inactivated can be obtained. However, a method of producing the microorganism of *Corynebacterium* genus according to the current embodiment of the present invention is not limited to the homologous recombination, and can be any method known to those of ordinary skill in the art.

The microorganism of *Corynebacterium* genus may be *Corynebacterium glutamicum* KFCC 10881-CJP5101 (Accession number KCCM-10708P).

The present invention also provides a method of producing L-lysine according to an embodiment of the present invention, the method comprising: culturing the microorganism of *Corynebacterium* genus to produce L-lysine in cultures or cells; and collecting L-lysine from the cultures.

In the method of producing L-lysine according to the current embodiment of the present invention, the microorganism of *Corynebacterium* genus may be cultured using any culture conditions and methods known to those of ordinary skill in the art. An example of a culture medium for culturing the microorganism of *Corynebacterium* genus may be the culture medium disclosed in the Manual of Methods for General Bacteriology by the American Society for Bacteriology (Washington D.C., USA, 1981). Carbohydrate sources that can be used in the medium include the following: sugars and carbohydrates such as glucose, saccharose, lactose, fructose, maltose, starch and cellulose; oils and fats such as soybean oil, sunflower oil, castor oil, and coconut oil; fatty acids such as palmitic acid, stearic acid and linolenic acid; alcohols such as glycerol, ethanol; and organic acids such as acetic acid. The sugar sources mentioned above can be used alone or in combination. Examples of nitrogen sources include the following: peptone, yeast extracts, meat extracts, malt extracts, corn steep liquor, soybean meal, and urea or inorganic compounds such as ammonium sulfate, ammonium chloride, ammonium phosphate, ammonium carbonate, and ammonium nitrate. The nitrogen sources mentioned above also can be used alone or in combination. Examples of phosphorus sources include the following: potassium dihydrogen phosphate, dipotassium hydrogen phosphate, or corresponding sodium salts thereof. Also, the culture medium can include metal salts, such as magnesium sulfate or iron sulfate, which is necessary for growth. In addition, essential materials for growth such as amino acids and vitamins can be used in addition to the above ingredients. Moreover, proper precursors can be used in the culture medium. The above ingredients can be added to the culture medium during the cultivation in a batchwise or continuous manner.

The pH of the culture can be controlled using a basic compound such as sodium hydroxide, potassium hydroxide or ammonia, or an acid compound such as phosphoric acid or sulfuric acid. Also, the use of an antifoaming agent such as fatty acid polyglycol ester can suppress foam generation. Oxygen or an oxygen-containing gas such as air can be injected into the culture in order to maintain aerobic condition. The temperature of the culture may be 20 to 45° C., preferably 25 to 40° C. The culturing can be performed until a desired quantity of L-lysine is produced, but the culturing is desirably performed for 10 to 160 hours.

The culture can be performed in a continuous manner using a batch, fed batch, repeated fed batch or batchwise method. These methods are well known to those of ordinary skill in the art, and the present invention is not limited thereto.

L-amino acid may be separated and analyzed by anion exchange chromatography and then ninhydrin derivatization.

To develop the microorganism of *Corynebacterium* genus and the method of producing L-lysine using the same, the inventors of the present invention performed an experiment such that *Corynebacterium glutamicum* ATCC 13032 was cultured in the presence of L-lysine, proteins expressed therefrom were analyzed by two-dimensional electrophoresis, and then the obtained results were compared with the results obtained from a control experiment performed by culturing the microorganism in the absence of L-lysine to analyze protein obtained therefrom. As a result, proteins overexpressed in the presence of L-lysine, that is, proteins for which the expression thereof was supposed to be induced by L-lysine, were confirmed. Based on information on the obtained proteins, it was confirmed that the proteins were NCgl1835, NCgl2053 and the like by confirming the information on the above proteins from National Institutes of Health (NIH) GenBank.

In addition, whether the expression of the genes was really induced in the presence of L-lysine was confirmed. First, nucleic acid regions supposed as a promoter part of the genes were amplified by a polymerase chain reaction (PCR). Then, the amplified promoter nucleic acid was fused with a lacZ gene in which a promoter was removed to prepare a promoter of the genes –lacZ fusion gene. Thereafter, the obtained fusion gene was inserted into a vector, a microorganism was transformed with the vector, the transformed microorganism was cultured in the presence of L-lysine to confirm whether the lacZ protein was expressed by assaying beta-galactosidase activity. As a result, it was confirmed that the expression of the genes was really induced by L-lysine.

However, how these genes affect L-lysine biosynthesis by L-lysine producing microorganism was unknown. Besides confirming the genes, the inventors of the present invention measured L-lysine production by inactivating endogenous NCgl1835 genes of the microorganism of *Corynebacterium* genus, and confirmed that L-lysine production ability was improved.

Hereinafter, the present invention will be described in further detail with reference to the following examples. These examples are for illustrative purposes only, and are not intended to limit the scope of the present invention.

EXAMPLES

In the following examples, in order to confirm how the NCgl1835 gene for which the expression thereof was induced in the presence of L-lysine affects L-lysine production, L-lysine production was measured by inactivating endogenous NCgl1835 genes of *Corynebacterium glutamicum* KFCC10881 and culturing the microorganism.

Example 1

Vector Preparation for Inactivating Endogenous NCgl1835 Gene of the Microorganism of *Corynebacterium* Genus To prepare a vector including a part of the NCgl1835 gene sequence and an antibiotic marker, a PCR was performed using oligonucleotide of SEQ ID Nos: 3 and 4 as a primer and using chromosome DNA of *Corynebacterium glutamicum* ATCC 13032 as a template to amplify about 500 bp (SEQ ID NO: 2) of a NCgl1835 gene segment (129-628 nucleotide of SEQ ID NO: 1). The PCR was repeated thirty times by performing denaturation at 96° C. for 30 seconds, annealing at 52° C. for 30 seconds, and polymerization at 72° C. for 30 seconds. The amplified NCgl1835 gene segment was cloned into an *E. coli* plasmid pCR2.1 using TOPO Cloning Kit (Invitrogen, USA) to obtain a pCR-1835 plasmid. FIG. 1 illustrates a pCR-1835 vector into which about 500 bp of the NCgl1835 gene segment is cloned.

Example 2

Preparation of L-Lysine Producing Microorganism in which Endogenous NCgl1835 Gene of *Corynebacterium glutamicum* KFCC10881 is Inactivated Using transformation disclosed in Appl. Microbiol. Biotechnol. (1999) 52:541-545, the pCR-1835 plasmid prepared by Example 1 was transformed into *Corynebacterium glutamicum* KFCC10881, a L-lysine producing microorganism, using an electric pulse method. To confirm whether NCgl1835 genes were disrupted in the transformed microorganism, a PCR was performed using a chromosome DNA of the transformed microorganism obtained 2 days after culture. The PCR was performed using chromosome DNA of the transformed microorganism as a template and oligonucleotide of SEQ ID Nos: 5 and 6 as a primer to amplify about 5,040 bp of a NCgl1835 gene segment (100-671 nucleotide of SEQ ID NO: 1) including the pCR-1835 plasmid. As a result, due to crossing over by homologous recombination, the pCR-1835 plasmid was inserted into a middle part of the endogenous NCgl1835 gene on the chromosome DNA to obtain a microorganism confirming that the NCgl1835 gene was disrupted. The microorganism was named *Corynebacterium glutamicum* KFCC10881-CJ P5101.

*Corynebacterium glutamicum* KFCC10881-CJP5101 was deposited on Nov. 16, 2005 at the Korean Culture Center of Microorganisms (KCCM) under the Budapest Convention, and had Accession No. KCCM-10708P.

Example 3

L-Lysine Production Using *Corynebacterium glutamicum* KFCC10881-CJP5101

*Corynebacterium glutamicum* KFCC10881-CJP5101 prepared in Example 2 was cultured to produce L-lysine.

First, *Corynebacterium glutamicum* KFCC10881, which was parent strain, and *Corynebacterium glutamicum* KFCC10881-CJP5101 were inoculated into a 250 ml corner-baffled flask including 25 ml of the seed medium below, and then cultured at 30° C. for 20 hours while stirred at 200 rpm. 1 ml of the obtained seed culture solution was inoculated into a 250 ml corner-baffled flask including 24 ml of the production medium below, and then cultured at 30° C. for 120 hours while stirred at 200 rpm. After culture was terminated, L-lysine production was measured by high performance liquid chromatography (HPLC, Waters 2457). As a result, amounts of L-lysine in the culture of *Corynebacterium glutamicum* KFCC10881 and *Corynebacterium glutamicum* KFCC10881-CJP5103 were represented as hydrochloride salt of the L-lysine and were 45 g/l and 50 g/l, respectively.

Seed Medium (pH 7.0):

20 g of raw sugar, 10 g of peptone, 5 g of yeast extract, 1.5 g of urea, 4 g of $KH_2PO_4$, 8 g of $K_2HPO_4$, 0.5 g of $MgSO_4$ $7H_2O$, 100 μg of biotin, 1,000 μg of thiamine HCl, 2,000 μg of calcium pantothenate, 2,000 μg of nicotin amide (1 L of distilled water basis)

Production Medium (pH 7.0):

100 g of raw sugar, 40 g of $(NH_4)_2SO_4$, 2.5 g of soy protein, 5 g of corn steep solids, 3 g of urea, 1 g of $KH_2PO_4$, 0.5 g of $MgSO_4$ $7H_2O$, 100 μg of biotin, 1,000 μg of thiamine HCl, 2,000 μg of calcium pantothenate, 3,000 μg of nicotin amide, 30 g of $CaCO_3$ (1 L of distilled water basis)

Example 4

L-Lysine Collection from a Culture of *Corynebacterium glutamicum* KFCC10881-CJP5101

By adding hydrochloric acid to 1 L of a lysine fermentation broth obtained by culturing *Corynebacterium glutamicum* KFCC10881-CJP5101 in a medium containing molasses and raw sugar, the pH of the fermentation broth was adjusted to pH 2.0, and Ca ions were transformed into $CaSO_4$ and $CaCl_2$. Then, the culture was absorbed into a cation exchange resin (Diaion SK-L10), which was reproduced in the form of ammonium, by flowing the culture in the upward direction. After residual bacteria within the cation exchange resin were removed by washing with demineralized water, the high-concentrated L-lysine was collected by eluting the resin with 2N ammonium hydroxide. The collected solution was concentrated and crystallized by cooling to 20° C., while adjusting the pH to 5.0. A first wet product was obtained by centrifugal separation of a crystallization-completed slurry and a second wet product was obtained by batch concentrating and crystallizing the mother solution. 47.5 g of a dried L-lysine product with 98.5% L-lysine content was obtained by combining the first and second wet products and drying the combined product.

In the microorganism of *Corynebacterium* genus according to the present invention, since the endogenous NCgl1835 gene of the microorganism is inactivated, L-lysine production ability thereof is improved.

According to the present invention, L-lysine can be produced with high productivity.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microorganism of *Corynebacterium glutamicum* that has an inactivated endogenous NCgl1835 gene therein and produces L-lysine, wherein the NCgl1835 gene has a nucleotide sequence of SEQ ID NO: 1 and the inactivated endogenous Ncgl1835 gene is obtained by mutation of the nucleotide sequence of SEQ ID NO: 1, wherein the microorganism is *Corynebacterium glutamicum* KFCC10881-CJP5101 (Accession No. KCCM-10708P).

2. A method of producing L-lysine comprising:
culturing a microorganism of *Corynebacterium glutamicum* that has an inactivated endogenous NCgl1835 gene therein and produces L-lysine, wherein the NCgl1835 gene has a nucleotide sequence of SEQ ID NO: 1 and the inactivated endogenous Ncgl1835 gene is obtained by mutation of the nucleotide sequence of SEQ ID NO:1 to produce L-lysine in cultures or cells; and collecting L-lysine from the cultures.

* * * * *

SEQUENCE LISTING

<160> NUMBER OF SEQ ID NOS: 6

<210> SEQ ID NO 1
<211> LENGTH: 753
<212> TYPE: DNA

<213> ORGANISM: Corynebacterium glutamicum ATCC 13032
<220> FEATURE:
<221> NAME/KEY: gene
<222> LOCATION: (1)..(753)
<223> OTHER INFORMATION: NCgl1835 gene

<400> SEQUENCE: 1

```
atgactgaga ctggatttgg aattgatatc ggtggctccg gcatcaaagg cgcccgcgtt    60
aaccttaaga ccggtgagtt tattgatgaa cgcataaaaa tcgccacccc taagccagca   120
accccagagg ctgtcgccga agtagtcgca gagattattt ctcaagccga atgggagggt   180
ccggtcggaa ttaccctgcc gtcggtcgtt cgcgggcaga tcgcgctatc cgcagccaac   240
attgacaagt cctggatcgg caccgatgtg cacgaacttt tgaccgcca cctaaatggc   300
cgagagatca ccgttctcaa tgacgcagac gccgccggca tcgccgaagc aacctttggc   360
aaccctgccg cacgcgaagg cgcagtcatc ctgctgaccc ttggtacagg tattggatcc   420
gcattccttg tggatggcca actgttcccc aacacagaac tcggtcacat gatcgttgac   480
ggcgaggaag cagaacacct tgcagcagca tccgtcaaag aaaacgaaga tctgtcatgg   540
aagaaatggg cgaagcacct gaacaaggtg ctgagcgaat acgagaaact tttctcccca   600
tccgtcttca tcatcggtgg cggaatttcc agaaagcacg aaaagtggct tccattgatg   660
gagctagaca ctgacattgt cccagctgag ctgcgcaatc gagccggaat cgtaggagct   720
gccatggcag taaaccaaca cctcacccca taa                                753
```

<210> SEQ ID NO 2
<211> LENGTH: 500
<212> TYPE: DNA
<213> ORGANISM: Artificial Sequence
<220> FEATURE:
<223> OTHER INFORMATION: a segment of NCgl1835 for the construction of disruption vector

<400> SEQUENCE: 2

```
ggctgtcgcc gaagtagtcg cagagattat ttctcaagcc gaatgggagg gtccggtcgg    60
aattaccctg ccgtcggtcg ttcgcgggca gatcgcgcta tccgcagcca acattgacaa   120
gtcctggatc ggcaccgatg tgcacgaact ttttgaccgc cacctaaatg ccgagagat   180
caccgttctc aatgacgcag acgccgccgg catcgccgaa gcaacctttg caaccctgc   240
cgcacgcgaa ggcgcagtca tcctgctgac ccttggtaca ggtattggat ccgcattcct   300
tgtggatggc caactgttcc ccaacacaga actcggtcac atgatcgttg acggcgagga   360
agcagaacac cttgcagcag catccgtcaa agaaaacgaa gatctgtcat ggaagaaatg   420
ggcgaagcac ctgaacaagg tgctgagcga atacgagaaa cttttctccc catccgtctt   480
catcatcggt ggcggaattt                                                500
```

<210> SEQ ID NO 3
<211> LENGTH: 20
<212> TYPE: DNA
<213> ORGANISM: Artificial Sequence
<220> FEATURE:
<223> OTHER INFORMATION: primer 1 for amplifying a partial region (129-628nt) of NCgl1835 gene

<400> SEQUENCE: 3

```
ggctgtcgcc gaagtagtcg                                                 20
```

<210> SEQ ID NO 4
<211> LENGTH: 20

-continued

```
<212> TYPE: DNA
<213> ORGANISM: Artificial Sequence
<220> FEATURE:
<223> OTHER INFORMATION: primer 2 for amplifying a partial
      region(129-628nt) of NCgl1835 gene

<400> SEQUENCE: 4
aaattccgcc accgatgatg                                                 20

<210> SEQ ID NO 5
<211> LENGTH: 20
<212> TYPE: DNA
<213> ORGANISM: Artificial Sequence
<220> FEATURE:
<223> OTHER INFORMATION: primer 3 for amplifying a partial region
      (100-671nt) of NCgl1835 gene

<400> SEQUENCE: 5
atcgccaccc ctaagccagc                                                 20

<210> SEQ ID NO 6
<211> LENGTH: 20
<212> TYPE: DNA
<213> ORGANISM: Artificial Sequence
<220> FEATURE:
<223> OTHER INFORMATION: primer 4 for amplifying a partial
      region(100-671nt) of NCgl1835 gene

<400> SEQUENCE: 6
gtgtctagct ccatcaatgg                                                 20
```